(12) United States Patent
Hon

(10) Patent No.: US 9,370,205 B2
(45) Date of Patent: *Jun. 21, 2016

(54) ELECTRONIC CIGARETTE

(71) Applicant: FONTEM HOLDINGS 1 B.V., Amsterdam (NL)

(72) Inventor: Lik Hon, North Point (HK)

(73) Assignee: Fontem Holdings 1 B.V., Amsterdam (NL)

(*) Notice: Subject to any disclaimer, the term of this patent is extended or adjusted under 35 U.S.C. 154(b) by 27 days.

This patent is subject to a terminal disclaimer.

(21) Appl. No.: 13/754,521

(22) Filed: Jan. 30, 2013

(65) Prior Publication Data

US 2013/0139833 A1    Jun. 6, 2013

Related U.S. Application Data

(63) Continuation of application No. 12/226,819, filed as application No. PCT/CN2007/001576 on May 15, 2007, now Pat. No. 8,375,957.

(30) Foreign Application Priority Data

May 16, 2006  (CN) .................. 2006 2 0090805 U

(51) Int. Cl.
  *A24F 47/00* (2006.01)
  *H05B 1/02* (2006.01)
  (Continued)

(52) U.S. Cl.
  CPC ............ *A24F 47/008* (2013.01); *A24F 47/002* (2013.01); *A24F 47/004* (2013.01); *F22B 1/284* (2013.01); *H01M 2/1055* (2013.01); *H01M 10/425* (2013.01); *H01M 10/46* (2013.01);
  (Continued)

(58) Field of Classification Search
  CPC .. A24F 47/0008; A24F 47/002; A24F 47/004
  See application file for complete search history.

(56) References Cited

U.S. PATENT DOCUMENTS 705,919 A    7/1902  Gill
1,775,947 A    9/1930  Robinson
(Continued)

FOREIGN PATENT DOCUMENTS

CA    2562581 A1    10/2005
CA    2647212       5/2006
(Continued)

OTHER PUBLICATIONS

PRB of the State Intellectual Patent Office, Decision of Patent Invalidation Petition (No. 22179) issued in Chinese Patent Application No. 200620090805.0 (Mar. 3, 2014).
(Continued)

*Primary Examiner* — Michael H Wilson
*Assistant Examiner* — Dionne Walls Mayes
(74) *Attorney, Agent, or Firm* — Kenneth H. Ohriner; Perkins Coie LLP

(57) ABSTRACT

An electronic cigarette includes a battery assembly, an atomizer assembly and a cigarette bottle assembly. An external thread electrode is located in one end of battery assembly. An internal thread electrode is located in one end of atomizer assembly. The battery assembly and the atomizer assembly are connected by the screwthread electrode. The cigarette bottle assembly is inserted into the other end of the atomizer assembly and both form a cigarette type or cigar type body.

22 Claims, 10 Drawing Sheets

(51) Int. Cl.
  *H05B 3/06* (2006.01)
  *H05B 3/42* (2006.01)
  *F22B 1/28* (2006.01)
  *H01M 2/10* (2006.01)
  *H01M 10/42* (2006.01)
  *H01M 10/46* (2006.01)
  *H02J 7/00* (2006.01)

(52) U.S. Cl.
  CPC ............ *H02J7/0042* (2013.01); *H02J 7/0052* (2013.01); *H05B 1/0244* (2013.01); *H05B 1/0297* (2013.01); *H05B 3/06* (2013.01); *H05B 3/42* (2013.01)

(56) References Cited

U.S. PATENT DOCUMENTS

| | | |
|---|---|---|
| 2,057,353 A | 10/1936 | Whittemore |
| 2,631,219 A | 3/1953 | Suchy |
| 3,200,819 A | 8/1965 | Gilbert |
| 3,551,643 A | 12/1970 | Pricenski et al. |
| 4,171,000 A | 10/1979 | Uhle |
| 4,207,457 A | 6/1980 | Haglund et al. |
| 4,228,925 A | 10/1980 | Mendelovich |
| 4,641,053 A | 2/1987 | Takeda |
| 4,735,217 A | 4/1988 | Gerth et al. |
| 4,756,318 A | 7/1988 | Clearman et al. |
| 4,771,796 A | 9/1988 | Myer |
| 4,819,665 A | 4/1989 | Roberts et al. |
| 4,848,374 A | 7/1989 | Chard et al. |
| 4,945,929 A | 8/1990 | Egilmex |
| 4,945,931 A | 8/1990 | Gori |
| 4,947,875 A | 8/1990 | Brooks |
| 5,042,470 A | 8/1991 | Kanesaka |
| 5,060,671 A | 10/1991 | Counts et al. |
| 5,080,114 A | 1/1992 | Rudolph et al. |
| 5,095,921 A | 3/1992 | Losee et al. |
| 5,144,962 A | 9/1992 | Counts et al. |
| 5,159,940 A | 11/1992 | Hayward et al. |
| 5,190,060 A | 3/1993 | Gerding et al. |
| 5,224,498 A | 7/1993 | Deevi et al. |
| 5,249,586 A | 10/1993 | Morgan et al. |
| 5,261,424 A | 11/1993 | Sprinkel, Jr. |
| 5,285,798 A | 2/1994 | Banerjee et al. |
| 5,322,075 A | 6/1994 | Deevi et al. |
| 5,388,594 A | 2/1995 | Counts et al. |
| 5,438,978 A | 8/1995 | Hardester, III |
| 5,497,791 A | 3/1996 | Bowen et al. |
| 5,505,214 A | 4/1996 | Collins et al. |
| 5,591,368 A | 1/1997 | Fleischhauer et al. |
| 5,666,977 A | 9/1997 | Higgins et al. |
| 5,666,978 A | 9/1997 | Counts et al. |
| 5,730,158 A | 3/1998 | Collins et al. |
| 5,743,251 A | 4/1998 | Howell et al. |
| 5,746,251 A | 5/1998 | Bullard |
| 5,799,663 A | 9/1998 | Gross et al. |
| 5,819,756 A | 10/1998 | Mielordt |
| 5,878,752 A | 3/1999 | Adams et al. |
| 5,894,841 A | 4/1999 | Voges |
| 6,040,560 A | 3/2000 | Fleischhauer et al. |
| 6,041,789 A | 3/2000 | Bankert et al. |
| 6,095,153 A | 8/2000 | Kessler et al. |
| 6,164,287 A | 12/2000 | White |
| 6,178,969 B1 | 1/2001 | St. Charles |
| 6,196,218 B1 | 3/2001 | Voges |
| 6,354,293 B1 | 3/2002 | Madison |
| 6,357,671 B1 | 3/2002 | Cewers |
| 6,443,146 B1 | 9/2002 | Voges |
| 6,532,965 B1 | 3/2003 | Abhulimen et al. |
| 6,601,776 B1 | 8/2003 | Oljaca |
| 6,715,494 B1 | 4/2004 | McCoy |
| 6,772,756 B2 | 8/2004 | Shayan |
| 6,803,545 B2 | 10/2004 | Blake et al. |
| 6,810,883 B2 | 11/2004 | Felter et al. |
| 6,854,461 B2 | 2/2005 | Nichols et al. |
| 7,100,618 B2 | 9/2006 | Dominguez |
| 7,131,599 B2 | 11/2006 | Katase |
| 7,726,320 B2 | 6/2010 | Robinson et al. |
| 7,832,410 B2 | 11/2010 | Hon |
| 7,845,359 B2 | 12/2010 | Montaser |
| 7,997,280 B2 | 8/2011 | Rosenthal |
| 8,156,944 B2 | 4/2012 | Hon |
| 2003/0108342 A1 | 6/2003 | Sherwood et al. |
| 2004/0182403 A1 | 9/2004 | Andersson et al. |
| 2004/0261802 A1 | 12/2004 | Griffin et al. |
| 2005/0016550 A1 | 1/2005 | Katase |
| 2005/0236006 A1 | 10/2005 | Cowan |
| 2006/0196518 A1 | 9/2006 | Hon |
| 2007/0267031 A1 | 11/2007 | Hon |
| 2008/0257367 A1 | 10/2008 | Paterno |
| 2008/0276947 A1 | 11/2008 | Martzel |
| 2009/0095311 A1 | 4/2009 | Han |
| 2009/0151717 A1 | 6/2009 | Bowen et al. |
| 2009/0188490 A1 | 7/2009 | Han |
| 2009/0230117 A1 | 9/2009 | Fernando et al. |
| 2009/0260642 A1 | 10/2009 | Monsees et al. |
| 2009/0272379 A1 | 11/2009 | Thorens et al. |
| 2010/0031968 A1 | 2/2010 | Sheikh et al. |
| 2010/0126505 A1 | 5/2010 | Rinker |
| 2010/0181387 A1 | 7/2010 | Zaffaroni et al. |
| 2010/0200008 A1 | 8/2010 | Taieb |
| 2010/0242974 A1 | 9/2010 | Pan |
| 2010/0307518 A1 | 12/2010 | Wang |
| 2011/0005535 A1 | 1/2011 | Xiu |
| 2011/0011396 A1 | 1/2011 | Fang |
| 2011/0036346 A1 | 2/2011 | Cohen et al. |

FOREIGN PATENT DOCUMENTS

| | | |
|---|---|---|
| CH | 1191696 A | 9/1998 |
| CH | 1530041 A | 9/2004 |
| CN | 2047485 U | 11/1989 |
| CN | 2084236 U | 9/1991 |
| CN | 1135860 | 11/1996 |
| CN | 1196660 A | 11/1996 |
| CN | 2293957 Y | 10/1998 |
| CN | 1252961 A | 5/2000 |
| CN | 1575673 A | 5/2000 |
| CN | 1106812 C | 4/2003 |
| CN | 1541577 A | 11/2004 |
| CN | 2719043 Y | 8/2005 |
| CN | 2777995 Y | 5/2006 |
| CN | 2887086 U | 4/2007 |
| CN | 101116542 A | 2/2008 |
| CN | 101176805 A | 5/2008 |
| CN | 201067079 Y | 6/2008 |
| CN | 201079011 | 7/2008 |
| CN | 201379072 Y | 1/2010 |
| CN | 201797997 U | 4/2011 |
| CN | 202026802 U | 11/2011 |
| CN | 202026804 U | 11/2011 |
| DE | 10051792 A1 | 5/2002 |
| EP | 0057243 A1 | 8/1982 |
| EP | 0230420 A1 | 8/1987 |
| EP | 0295122 B1 | 12/1988 |
| EP | 0342538 A2 | 11/1989 |
| EP | 0358002 A2 | 3/1990 |
| EP | 0545186 A2 | 6/1993 |
| EP | 0703735 A1 | 4/1996 |
| EP | 0824927 A2 | 2/1998 |
| EP | 0845220 A1 | 6/1998 |
| EP | 0893071 A1 | 1/1999 |
| EP | 0951219 A1 | 10/1999 |
| EP | 01618803 A1 | 1/2006 |
| EP | 01618808 A1 | 1/2006 |
| EP | 01736065 A1 | 12/2006 |
| GB | 1528391 A | 10/1978 |
| JP | 64000498 U | 1/1989 |
| JP | 06114105 A | 4/1994 |
| JP | 07506999 | 8/1995 |
| JP | 09075058 A | 3/1997 |
| UA | 47514 | 12/1997 |
| WO | WO-9409842 A1 | 5/1994 |
| WO | WO9421317 | 9/1994 |

(56) References Cited

FOREIGN PATENT DOCUMENTS

| WO | WO-9421317 A1 | 9/1994 |
|---|---|---|
| WO | WO-9740876 A2 | 11/1997 |
| WO | WO-9748293 A1 | 12/1997 |
| WO | WO-9817130 A1 | 4/1998 |
| WO | WO-0049901 A2 | 8/2000 |
| WO | WO-0050111 A1 | 8/2000 |
| WO | WO-0105459 A1 | 1/2001 |
| WO | WO-03022364 A1 | 3/2003 |
| WO | WO-03034847 A1 | 5/2003 |
| WO | WO-03055486 A1 | 7/2003 |
| WO | WO-03101454 A1 | 12/2003 |
| WO | WO-04001407 A1 | 12/2003 |
| WO | WO-2004023222 | 3/2004 |
| WO | WO-2004080216 | 9/2004 |
| WO | WO2005099494 | 10/2005 |
| WO | WO-2006082571 | 8/2006 |
| WO | WO-2007078273 | 7/2007 |
| WO | WO-2008077271 | 7/2008 |
| WO | WO-2008130813 | 10/2008 |
| WO | WO-2009118085 | 10/2009 |
| WO | WO-2009135729 | 11/2009 |
| WO | WO-2010052323 | 5/2010 |
| WO | WO-2010145468 | 12/2010 |
| WO | WO-2010145805 | 12/2010 |
| WO | WO-2011010334 | 1/2011 |
| WO | WO-2011022431 | 2/2011 |

OTHER PUBLICATIONS

State Intellectual Property Office of the People's Republic of China, Examination Decision of the Patent Re-examination Board on the Invalidity Declaration Application re Chinese Patent Application No. 200620090805.0 (Jun. 23, 2010).
CB Distributors Inc. and DR Distributors, LLC , Petition for Inter Partes Review of U.S. Pat. No. 8,156,944 and Exhibits 1-20, filed Jun. 27, 2013.
European Patent Office, Supplementary European Search Report and Search Opinion for EP 10740882.5, Oct. 16, 2013.
European Patent Office, Third Party Observation for EP Application No. 10740882, filed by Anonymous on Oct. 3, 2013.
IP Australia, Patent Examination Report No. 1 for AU 2010213240, Aug. 5, 2013.
Pan, Fenglin—Request for Invalidation of CN200720148285.9 in Chinese, along with English translation of same.
Pan, Fenglin - Request for Invalidation of CN200920001296.3 in Chinese, along with English translation of same.
State Intellectual Property Office, P.R. China, Office Action for CN201080016105.6, Aug. 30, 2013, with English translation.
Australian Patent Office, Examination Report for SG 200505930-8, May 4, 2006.
Australian Patent Office; Exam Report for AU2004234199, Aug. 14, 2009.
Australian Patent Office; Search and Examination Report for SG200604498-6, Apr. 16, 2008.
Australian Patent Office; Singapore Examination Report for Singapore Patent Application No. 0604498-6 SG 200505930-8, May 13, 2008.
CN Creative ; *INTELLICIG USA, Ruyan* v. *Smoking Everywhere et al.* CV11-6268 Invalidity Contentions, Apr. 12, 2012.
Cyphert, GIL DBA NU1S, *Ruyan* v. *Smoking Everywhere et al.* CV11-0367 Invalidity Contentions, Apr. 11, 2012.
European Patent Office, extended European Search Report for EP 07721148, Dec. 6, 2010.
European Patent Office, extended European Search Report for EP 11001479, Jul. 4, 2011.
European Patent Office, Supplementary European Search Report for EP04718242, Jul. 27, 2007.
European Patent Office, Supplementary European Search Report for EP05729107, Jul. 31, 2007.
European Patent Office, Supplementary Partial European Search Report for EP04718242, May 22, 2007.

European Patent Office, Supplementary Partial European Search Report for EP05729107, May 22, 2007.
FIN Branding Group, LLC, Request for Inter Partes Reexamination of U.S. Pat. No. 8,156,944, filed Sep. 13, 2012.
FIN Branding Group, LLC, Submission of Prior Art and Miscellaneous Statement Pursuant to 376 C.F.R. §1.948, Feb. 27, 2013.
IP Australia, Patent Examination Report No. 1 for AU2007250367, Jul. 30, 2012.
IP Australia, Patent Examination Report No. 1 for AU2007250368, Aug. 9, 2012.
Japanese Patent Office; Office Action for JP2006504199, Oct. 30, 2009.
Korean Patent Office; Notice of Preliminary Rejection for KR1020057009767, Jul. 27, 2009.
Macau Patent Office; Official Communication for MOI121, Apr. 17, 2009.
Machine translation Chinese Patent Application 200420031182 which corresponds to the priority document of WO20051099494 (Hon '494) Oct. 27, 2005, cited in Nov. 27, 2012 Office Action identified above.
Machine translation of Chinese Patent Application 03111582.9 which corresponds to the priority document of WO2004/095955 (Hon '955) Nov. 11, 2004, cited in the Nov. 27, 2012 Office Action identified above.
Malaysia Intellectual Property Office; Examiners Report for Malaysian Application No. PI 20041407, Sep. 28, 2007.
Manual for Electric Engineers, 2nd Edition, Mar. 2000.
Manual for Mechanical Designers, 4th Edition, Jan. 2002.
Materials Manual—Nonmetal, Jul. 1985.
*Sottera, Inc., Ruyan* v. *Smoking Everywhere et al.* CV11-0367 Invalidity Contentions, Apr. 12, 2012.
*Sottera, Inc., Ruyan* v. *Smoking Everywhere et al.* CV11-0367 Invalidity Contentions, Exhibit 7 (Claim 20 Claim Chart), Apr. 12, 2012.
*Sottera, Inc., Ruyan* v. *Smoking Everywhere et al.* CV11-0367 Invalidity Contentions, Exhibit 8 (Claim 24 Claim Chart), Apr. 12, 2012.
State Intellectual Property Office (China), English Translation of the Written Opinion for PCT/CN07/001575, Jul. 20, 2007.
State Intellectual Property Office (China), English Translation of the Written Opinion for PCT/CN07/001576, Aug. 3, 2007.
State Intellectual Property Office (China), International Search Report for International Application No. PCT/CN2004000182, Jun. 10, 2004.
State Intellectual Property Office (China), International Search Report for International Application No. PCT/CN2005/000337, Jul. 14, 2005.
State Intellectual Property Office (China), International Search Report for PCT/CN07/001575, Aug. 16, 2007.
State Intellectual Property Office (China), International Search Report for PCT/CN07/001576, Aug. 16, 2007.
State Intellectual Property Office International Search Report for PCT/CN10/073613, Aug. 26, 2010.
State Intellectual Property Office, International Search Report for PCT/CN10/000125, Apr. 1, 2010.
State Intellectual Property Office, Search Report for Utility Model Patent ZL 200620090805.0, Nov. 18, 2008.
Taiwan Intellectual Property Office; Official Letter for TW093111573, Apr. 24, 2009.
TechPowerUp, "What is a MOSFET, what does it look like, and how does it work?",http://www.techpowerup.com/articles/overclocking/voltmods/21, dated May 24, 2004, printed from the Internet of Jun. 4, 2011, 3 pages.
Ukrainian Patent Office; Examination Report for UA200511258, Feb. 4, 2009.
United States Patent and Trademark Office, Office Action in Inter Partes Reexamination of U.S. Pat. No. 8,156,944, mailed Nov. 27, 2012.
Chen, Zhiyong—English Translation of Claim Charts Accompanying Request to Invalidate CN Utility Model U.S. Pat. No. 200620090805.0 (citing D1-200420031182.0 and D2-CN 97190727.7), Jun. 6, 2013.
NJOY, Inc. et al., Defendants' Joint Invalidity Contentions, Case No. CV-14-01645 etc., Aug. 7, 2014.

(56) References Cited

OTHER PUBLICATIONS

NJOY, Inc. et al., Attachment D to Defendant's Joint Invalidity Contentions—Claim Charts for Patent 8375957, Aug. 7, 2014.
U.S. District Court, Central District of California, Western Division, Defendant NJOY, Inc.'s Vlemorandum of Points and Authorities in Support of Defendants' Motion for Leave to Amend Invalidity Contentions Dated Jun. 29, 2015 and tiled in Consolidated Case No. CV 14-01645 GW (MRW) and related consolidated cases.
U.S. District Court, Central District of California, Western Division, Defendant NJOY, Inc.'s Declaration of Brent K. Yamashita in Support of Defendants' Motion for Leave to Amend Invalidity Contentions dated 612912015 and filed in Consolidated Case No. CV 14-01645 GW (MRW) and related consolidated cases.
U.S. District Court, Central District of California, Western Division, Defendant NJOY, Inc.'s Exhibit 1 to Defendants' Motion for Leave to Amend Invalidity Contentions dated Jun. 29, 2015 and filed in Consolidated case No. CV 14-01645 GW (MRW) and related consolidated cases.
U.S. District Court, Central District of California, Western Division, Defendant NJOY, Inc.'s Exhibit 2 to Defendants' Motion for Leave to Amend Invalidity Contentions dated Jun. 29, 2015 and filed in Consolidated case No. CV 14-01645 GW (MRW) and related consolidated cases.
U.S. District Court, Central District of California, Western Division, Defendant NJOY, Inc.'s Exhibit 3 to Defendants' Motion for Leave to Amend Invalidity Contentions dated Jun. 29, 2015 and filed in Consolidated case No. CV 14-01645 GW (MRW) and related consolidated cases.
U.S. District Court, Central District of California, Western Division, Defendant NJOY, Inc.'s Exhibit 4 to Defendants' Motion for Leave to Amend Invalidity Contentions dated Jun. 29, 2015 and filed in Consolidated case No. CV 14-01645 GW (MRW) and related consolidated cases.
U.S. District Court, Central District of California, Western Division, Defendant NJOY, Inc.'s Exhibit 5 to Defendants' Motion for Leave to Amend Invalidity Contentions dated Jun. 29, 2015 and filed in Consolidated case No. CV 14-01645 GW (MRW) and related consolidated cases.
U.S. District Court, Central District of California, Western Division, Defendant NJOY, Inc.'s Reply Brief in Support of Defendants' Motion for Leave to Amend Invalidity Contentions dated Jul. 13, 2015 and filed in consolidated Case No. CV 14-01645 GW (MRW) and related consolidated cases.
U.S. District Court, Central District of California, Western Division, Defendant NJOY, Inc.'s Droduction documents VLACHOS 0000061-72; Consolidated Case No. CV 14-01645 GW (MRW) and related consolidated cases.
Collins, John M., Expert Report—Invalidrty, CV14-01845, Jun. 18, 2015.
Collins, John M., Expert Report—Invalidity, CV14-0 645—Appendix J-1 Invalidity Claim Chart for U.S. Pat. No. 8863752, Jun. 18, 2015.
Gowns, John M., Expert Report—Invalidity, CV14-01645—Appendix J-2 Invalidity Claim Chart for U.S. Pat. No. 8863752, Jun. 18, 2015.
Collins, John M., Expert Report—Invalidity, CV14-01645—Appendix J-3 Invalidity Claim Chart for U.S. Pat. No. 8863752, Jun. 18, 2015.
Collins, John M., Expert Report—Invalidity, CV14-01645—Appendix J-4 Invalidity Claim Chart for U.S. Pat. No. 8863752, Jun. 18, 2015.
Collins, John M., Expert Report—Invalidity, CV14-01645—Appendix J-5 Invalidity Claim Chart for U.S. Pat. No. 8863752, Jun. 18, 2015.
Collins, John M., Expert Report—Invalidity, CV14-01645—Appendix J-6 Invalidity Claim Chart for U.S. Pat. No. 8863752, Jun. 18, 2015.
Collins, John M., Expert Report—Invalidity, CV14-01645—Appendix F-1 Invalidity Claim Chart for U.S. Pat. No. 8375957, Jun. 18, 2015.
Collins, John M., Expert Report—Invalidity, CV14-01645—Appendix F-2 Invalidity Claim Chart for U.S. Pat. No. 8375957, Jun. 18, 2015.
Collins, John M., Expert Report—Invalidity, CV14-01645—Appendix F-3 Invalidity Claim Chart for U.S. Pat. No. 8375957, Jun. 18, 2015.
Collins, John M., Expert Report—Invalidity, CV14-01645—Appendix F-4 Invalidity Claim Chart for U.S. Pat. No. 8375957, Jun. 18, 2015.
Collins, John M., Expert Report—Invalidity, CV14-01645, Jun. 18, 2015—Exhibit 21, U.S. Pat. No. 2057353 Whittemore.
Collins, John M., Expert Report—Invalidity, CV14-01645, Jun. 18, 2015—Exhibit 22, U.S. Pat. No. 5894841 Voges.
Collins, John M., Expert Report—Invalidity, CV14-01645, Jun. 18, 2015—Exhibit 25, EP0845220B1 Susa.
Collins, John M., Expert Report—Invalidity, CV14-01645, Jun. 18, 2015—Exhibit 26, U.S. Pat. No. 3200819 Gilbert.
Collins, John M., Expert Report—Invalidity, CV14-01645, Jun. 18, 2015—Exhibit 63, U.S. Pat. No. 6196218 Voges '218.
Collins, John M., Expert Report—Invalidity, CV14-01645, Jun. 18, 2015—Exhibit 75, CA2752134 Hon '134.
Collins, John M., Expert Report—Invalidity, CV14-01645, Jun. 18, 2015—Exhibit 76, WO2005099494 Hon '494.
Collins, John M., Expert Report—Invalidity, CV14-01645, Jun. 18, 2015—Exhibit 77, CN2719043 Hon '043.
Collins, John M., Expert Report—Invalidity, CV14-01645, Jun. 18, 2015—Exhibit 78, TechPowerUp, www.techpowerup.com—"What is a MOSFET, what does it look like, and how does it work?"—published May 24, 2004.
Collins, John M., Expert Report—Invalidity, CV14-01645, Jun. 18, 2015—Exhibit 79, US20070267031 Hon '031.
Collins, John M., Expert Report—Invalidity, CV14-01645, Jun. 18, 2015—Exhibit 82, U.S. Pat. No. 705919 Gill.
Collins, John M., Expert Report—Invalidity, CV14-01645, Jun. 18, 2015—Exhibit 84, EP0845220A1 Susa.
Collins, John M., Expert Report—Invalidity, CV14-01645, Jun. 18, 2015—Exhibit 103, certified English translation of CN2719043 Hon '043 Translation.
Collins, John M., Expert Report—Invalidity, CV14-01645, Jun. 18, 2015—Exhibit 104, certified English translation of WO2005099494 Hon '494 Translation.
ITC Limited, Representation for Opposition to Grant of Patent against IN8529/DELNP/2008, May 11, 2015.
ITC Limited, Representation for Opposition to Grant of Patent against IN8529/DELNP/2008, May 11, 2015, D1—CN2719043.
ITC Limited, Representation for Opposition to Grant of Patent against IN8529/DELNP/2008, May 11, 2015, D1 Equivalent—EP1736065.
ITC Limited, Representation for Opposition to Grant of Patent against 1N8529/DELNP/2008, May 11, 2015, D2—WO1994021317.
Itc Limited, Representation for Opposition to Grant of Patent against IN8529/DELNP/2008, May 11, 2015, D3—US6601776.
ITC Limited, Representation for Opposition to Grant of Patent against IN8529/DELNP/2008, May 11, 2015, D4—EP01618803A.
IP Office India, First Examination Report for 8529/DELNP/2008, Jun. 25, 2015.
IP Office New Zealand, Exam Report for NZ572310, Apr. 29, 2010.
JT International S.A., Petition for Inter Partes Review of U.S. Pat. No. 8,375,957—IPR2015-01513, Paper 1, Jun. 26, 2015.
JT International S.A,, Petition for Inter Partes Review of U.S. Pat. No. 8,375,957—IPR2015-01513, Exhibit 1001, U.S. Pat. No. 8,375,957 to Hon , Jun. 26, 2015.
JT International S.A., Petition for Inter Partes Review of U.S. Pat. No. 8,375,957—IPR2015-01513, Exhibit 1002, Schuster Expert Declaration , Jun. 26, 2015.
JT International S.A., Petition for Inter Partes Review of U.S. Pat. No. 8,375,957—IPR2015-01513, Exhibit 1003, Canadian Patent Application No. 2 752 134 to Hon , Jun. 26, 2015.
JT International S.A., Petition for Inter Partes Review of U.S. Pat. No. 8,375,957—IPR2015-01513, Exhibit 1004, U.S. Pat. No. 6,234,167 to Cox , Jun. 26, 2015.

(56) References Cited

OTHER PUBLICATIONS

JT International S.A., Petition for Inter Partes Review of U.S. Pat. No. 8,375,957—IPR2015-01513, Exhibit 1005, EP 0 845 220 A1 to Susa, Jun. 26, 2015.
JT International S.A., Petition for Inter Partes Review of U.S. Pat. No. 8,375,957—IPR2015-01513, Exhibit 1006, U.S. Pat. No. 5,060,671 to Counts, Jun. 26, 2015.
JT International S.A., Petition for inter Partes Review of U.S. Pat. No. 8,375,957—IPR2015-01513, Exhibit 1007, U.S. Pat. No. 6,155,268 to Takeuchi, Jun. 26, 2015.
JT International S.A., Petition for Inter Partes Review of U.S. Pat. No. 8,375,957—IPR2015-01513, Exhibit 1008, WO 00/28843 A1 to Pienemann, Jun. 26, 2015.
JT International S.A., Petition for Inter Partes Review of U.S. Pat. No. 8,375,957—IPR2015-01513, Exhibit 1009, Certified English translation of WO 00/28843 A1 to Pienernann, Jun. 26, 2015.
JT International S.A., Petition for Inter Partes Review of U.S. Pat. No. 8,375,957—IPR2015-01513, Exhibit 1010, on 2719043 to Hon, Jun. 26, 2015.
JT International S.A., Petition for inter Partes Review of U.S. Pat. No. 8,375,957—IPR2015-01513, Exhibit 1011, Certified English translation of on 2719043 to Hon, Jun. 26, 2015.
JT International S.A., Petition for Inter Partes Review of U.S. Pat. No. 8,375,957—IPR2015-01513, Exhibit 1012, U.S. Pat. No. 2,057,353 to Whittemore, Jun. 26, 2015.
JT International S.A., Petition for Inter Partes Review of U.S. Pat. No. 8,375,957—IPR2015-01513, Exhibit 1013, U.S. Patent Publication No. 2003/0033055 A1 to McRae, Jun. 26, 2015.
JT International S.A., Petition for Inter Partes Review of U.S. Pat. No. 8,375,957—IPR2015-01513, Exhibit 1014, CN200620090805 to Hon, Jun. 26, 2015.
JT International S.A., Petition for Inter Partes Review of U.S. Pat. No. 8,375,957—IPR2015-01513, Exhibit 1015, Certified English translation of CN200620090805 to Hon, Jun. 26, 2015.
JT International S.A., Petition for Inter Partes Review of U.S. Pat. No. 8,375,957—IPR2015-01513, Exhibit 1016, Oct. 5, 2010 Office Action (957), Jun. 26, 2015.
JT International S.A., Petition for inter Partes Review of U.S. Pat. No. 8,375,957—IPR2015-01513, Exhibit 1017, Mar. 7, 2011 Response ('957), Jun. 26, 2015.
JT International S.A., Petition for Inter Partes Review of U.S. Pat. No. 8,375,957—IPR2015-01513, Exhibit 1018, Jun. 8, 2011 Office Action (957), Jun. 26, 2015.
JT International S.A., Petition for Inter Partes Review of U.S. Pat. No. 8,375,957—IPR2015-01513, Exhibit 1019, Dec. 8, 2011 Response ('957), Jun. 26, 2015.
JT International S.A., Petition for Inter Partes Review of U.S. Pat. No. 8,375,957—IPR2015-01513, Exhibit 1020, Jan. 9, 2012 Office Action ('957), Jun. 26, 2015.
JT International S.A., Petition for Inter Partes Review of U.S. Pat. No. 8,375,957—IPR2015-01513, Exhibit 1021, May 9, 2012 Response ('957), Jun. 26, 2015.
JT International S.A., Petition for Inter Partes Review of U.S. Pat. No. 8,375,957—IPR2015-01513, Exhibit 1022, Aug. 7, 2012 Office Action ('957), Jun. 26, 2015.
JT International S.A., Petition for Inter Partes Review of U.S. Pat. No. 8,375,957—IPR2015-01513, Exhibit 1023, Aug. 29, 2012 Response ('957), Jun. 26, 2015.
JT International S.A., Petition for Inter Partes Review of U.S. Pat. No. 8,375,957—IPR2015-01513, Exhibit 1024, Dec. 17, 2012 Notice of Allowance ('957), Jun. 26, 2015.
JT International S.A., Petition for Inter Partes Review of U.S. Pat. No. 8,375,957—IPR2015-01513, Exhibit 1025, McGraw-Hill Dictionary of Scientific and Technical Terms (5th ed. 1994), Jun. 26, 2015.
JT International S.A., Petition for Inter Partes Review of U.S. Pat. No. 8,375,957—IPR2015-01513, Exhibit 1026, Academic Press Dictionary of Science and Technology (1992), Jun. 26, 2015.
JT International S.A., Petition for Inter Partes Review of U.S. Pat. No. 8,375,957—IPR2015-01513, Exhibit 1027, American Heritage Dictionary of the English Language (1996), Jun. 26, 2015.
JT International S.A., Petition for Inter Partes Review of U.S. Pat. No. 8,375,957—IPR2015-01513, Exhibit 1028, KR 10-0469625 to Kim, Jun. 26, 2015.
JT International S.A., Petition for Inter Partes Review of U.S. Pat. No. 8,375,957—IPR2015-01513, Exhibit 1029, Certified English translation of KR 10-0469625 to Kim, Jun. 26, 2015.
JT International S.A., Petition for Inter Partes Review of U.S. Pat. No. 8,375,957—IPR2015-01513, Exhibit 1030, U.S. Pat. No. 1,446,087 to Griffin, Jun. 26, 2015.
JT International S.A., Petition for Inter Partes Review of U.S. Pat. No. 8,375,957—IPR2015-01513, Exhibit 1031, Curriculum Vitae of Jeffrey Arthur Schuster, Ph.D., Jun. 26, 2015.
JT International S.A., Petition for Inter Partes Review of U.S. Pat. No. 8,375,957—IPR2015-01513, Exhibit 1032, J.A, Speck, Mechanical Fastening, Joining and Assembly (1997), Jun. 26, 2015.
JT International S.A., Petition for Inter Partes Review of U.S. Pat. No. 8,375,957—IPR2015-01513, Exhibit 1033, U.S. Patent No. 705,919 to Gill, Jun. 26, 2015.
JT International S.A., Petition for Inter Partes Review of U.S. Pat. No. 8,375,957—IPR2015-01513, Exhibit 1034, U.S. Patent No. 980,830 to Patterson, Jun. 26, 2015.
JT International S.A., Petition for inter Partes Review of U.S. Pat. No. 8,375,957—IPR2015-01513, Exhibit 1035, U.S. Pat. No. 6,070,992 to Schnell, Jun. 26, 2015.
JT International S.A., Petition for Inter Partes Review of U.S. Pat. No. 8,375,957—IPR2015-01513, Exhibit 1036, U.S. Pat. No. 3,934,117 to Schladitz, Jun. 26, 2015.
JT International S.A., Petition for Inter Partes Review of U.S. Pat. No. 8,375,957—IPR2015-01513, Exhibit 1037, U.S. Pat. No. 4,531,178 to Uke, Jun. 26, 2015.
JT International S.A., Petition for Inter Partes Review of U.S. Pat. No. 8,375,957—IPR2015-01513, Exhibit 1038, U.S. Pat. No. 5,177,424 to Connors, Jun. 26, 2015.
JT International S.A., Petition for Inter Partes Review of U.S. Pat. No. 8,375,957—IPR2015-01513, Exhibit 1039, U.S. Pat. No. 6,232,784 to Dulasky, Jun. 26, 2015.
JT International S.A., Petition for Inter Partes Review of U.S. Pat. No. 8,863,752—IPR2015-01604, Paper 1, Jul. 20, 2015.
JT International S.A., Petition for Inter Partes Review of U.S. Pat. No. 8,863,752—IPR2015-01604, Exhibit 1001, U.S. Pat. No. 8,863,752 to Hon, Jul. 20, 2015.
JT International S.A., Petition for Inter Partes Review of U.S. Pat. No. 8,863,752—IPR2015-01604, Exhibit 1002, Declaration of Jeffrey A. Schuster, Ph,D., Jul. 20, 2015.
JT International S.A., Petition for Inter Partes Review of U.S. Pat. No. 8,863,752—IPR2015-01604, Exhibit 1003, U.S. Pat. No. 8,375,957 Certificate of Correction, Jul. 20, 2015.
JT International S.A., Petition for Inter Partes Review of U.S. Pat. No. 8,863,752—IPR2015-01604, Exhibit 1004, '752 Patent Application as Filed, Jul. 20, 2015.
JT International S.A., Petition for Inter Partes Review of U.S. Pat. No. 8,863,752—IPR2015-01604, Exhibit 1005, Restriction Requirement, Jul. 20, 2015.
JT International S.A., Petition for Inter Partes Review of U.S. Pat. No. 8,863,752—IPR2015-01604, Exhibit 1006, Response to Restriction Requirement, Jul. 20, 2015.
JT International S.A., Petition for Inter Partes Review of U.S. Pat. No. 8,863,752—IPR2015-01604, Exhibit 1007, Non-Final Office Action, Jul. 20, 2015.
JT International S.A., Petition for Inter Partes Review of U.S. Pat. No. 8,863,752—IPR2015-01604, Exhibit 1008, Response to Non-Final Office Action, July 20, 2015.
JT International S.A., Petition for Inter Partes Review of U.S. Pat. No. 8,863,752—IPR2015-01604, Exhibit 1009, Notice of Allowance, Jul. 20, 2015.
JT International S.A., Petition for Inter Partes Review of U.S. Pat. No. 8,863,752—IPR2015-01604, Exhibit 1010, McGraw-Hill Dictionary of Scientific and Technical Terms ("assembly") ("component") ("electrode") ("pore") ("porous") ("screwthread"), Jul. 20, 2015.
JT International S.A., Petition for Inter Partes Review of U.S. Pat. No. 8,863,752—IPR2015-01604, Exhibit 1011, American Heritage Dictionary ("atomize") ("flow"), Jul. 20, 2015.

(56) References Cited

OTHER PUBLICATIONS

JT International S.A., Petition for Inter Partes Review of U.S. Pat. No. 8,863,752—IPR2015-01604, Exhibit 1012, Merriam-Webster.com ("aerosol") ("atomizer") ("contain") ("housing") ("insert") ("paper") ("permeable") ("store"), Jul. 20, 2015.
JT International S.A., Petition for Inter Partes Review of U.S. Pat. No. 8,863,752—IPR2015-01604, Exhibit 1013, Academic Press Dictionary of Science and Technology ("permeability") ("solid"), Jul. 20, 2015.
JT International S.A., Petition for inter Partes Review of U.S. Pat. No. 8,863,752—IPR2015-01604, Exhibit 1014, Canadian Patent Application No. 2 752 134 to Hon, Jul. 20, 2015.
JT International S.A., Petition for Inter Partes Review of U.S. Pat. No. 8,863,752—IPR2015-01604, Exhibit 1015, U.S. Pat. No. 6,155,268 to Takeuchi, Jul. 20, 2015.
JT International S.A., Petition for Inter Partes Review of U.S. Pat. No. 8,863752—IPR2015-01604, Exhibit 1016, WO 00/28843 A1 to Pienernann, Jul. 20, 2015.
JT International S.A., Petition for Inter Partes Review of U.S. Pat. No. 8,863752—IPR2015-01604, Exhibit 1017, Certified English translation of WO 00/28843 A1 to Pienemann, Jul. 20, 2015.
JT International S.A., Petition for Inter Partes Review of U.S. Pat. No. 8,863,752—IPR2015-01604, Exhibit 1018, EP 0 845 220 A1 to Susa, Jul. 20, 2015.
JT International S.A., Petition for Inter Partes Review of U.S. Pat. No. 8,863,752—IPR2015-01604, Exhibit 1019, J.A. Speck, Mechanical Fastening ,Joining and Assembly (1997), Jul. 20, 2015.
Logic Technology Products, Inc., Petition for inter Partes Review of U.S. Pat. No. 8,375,957—IPR2015-00098, Oct. 21, 2014.
Logic Technology Products, Inc., Petition for Inter Partes Review of U.S. Pat. No. 8,375,957—IPR2015-00098, Exhibit 1001—U.S. Pat. No. 8,375,957, Oct. 21, 2014.
Logic Technology Products, Inc., Petition for Inter Partes Review of U.S. Pat. No. 8,375,957—IPFR2015-00098, Exhibit 1002, Declaration of Gregory Buckner, Ph.D., Oct. 21, 2014.
Logic Technology Products, Inc., Petition for inter Partes Review of U.S. Pat. No. 8,375,957—IPR2015-00098, Exhibit 1003, China Patent CN 2719043—issue date Aug. 24, 2005, Oct. 21, 2014.
Logic Technology Products, Inc., Petition for Inter Partes Review of U.S. Pat. No. 8,375,957—IPR2015-00098, Exhibit 1004, Certified English translation of CN 2719043 pursuant to 37 C.F.R. 42.63(b), Oct. 21, 2014.
Logic Technology Products, Inc., Petition for Inter Partes Review of U.S. Pat. No. 8,375,957—IPR2015-00098, Exhibit 1005, U.S. publication 2007/0267031 ("Hon '031"), which is the U.S. equivalent of CN 2719043, Oct. 21, 2014.
Logic Technology Products, Inc., Petition for inter Partes Review of U.S. Pat. No. 8,375,957—IPR2015-00098, Exhibit 1006, CA 2562581, which is the Canadian equivalent of CN 2719043, Oct. 21, 2014.
Logic Technology Products, Inc., Petition for Inter Partes Review of U.S. Pat. No. 8,375,957—IPR2015-00098, Exhibit 1007, U.S. Pat. No. 3,200,819 ("Gilbert")—issue date Aug. 17, 1965, Oct. 21, 2014.
Logic Technology Products, Inc., Petition for Inter Partes Review of U.S. Pat. No. 8,375,957—IPR2015-00098, Exhibit 1008, U.S. Pat. No. 2,057,353 ("Whittemore")—issue date Oct. 13, 1936, Oct. 21, 2014.
Logic Technology Products, Inc,, Petition for Inter Partes Review of U.S. Pat. No. 8,375,957—IPR2015-00098, Exhibit 1009, U.S. Pat. No. 5,894,841 ("Voges")—issue date Apr. 20, 1999, Oct. 21, 2014.
Logic Technology Products, Inc., Petition for Inter Partes Review of U.S. Pat. No. 8,375,957—IPR2015-00098, Exhibit 1010, U.S. Pat. App. Pub. 2008/0257367 ("Paterno")—filed Apr. 23, 2007, Oct. 21, 2014.
Logic Technology Products, Inc., Petition for Inter Partes Review of U.S. Pat. No. 8,375,957—IPR2015-00098, Exhibit 1011, EP 0533599A1 ("Connors")—publication date Mar. 24, 1993, Oct. 21, 2014.
Logic Technology Products, Inc., Petition for Inter Partes Review of U.S. Pat. No. 8,375,957—IPR2015-00098, Exhibit 1012, Non-patent publication "What is a MOSFET, what does it look like, and how does it work?" dated May 24, 2004, printed from the Internet Archive, i.e., the Wayback machine, which was archived on Mar. 5, 2010 ("TechPowerUp"), Oct. 21, 2014.
Logic Technology Products, Inc., Petition for Inter Partes Review of U.S. Pat. No. 8,375,957—IPR2015-00098, Exhibit 1013, Non-patent publication "What is a MOSFET, what does it look like, and how does it work?" dated May 24, 2004, printed from the Internet Archive, i.e., the Wayback machine, which was archived on Jul. 20, 2011 ("TechPowerUp"), Oct. 21, 2014.
Logic Technology Products, Inc., Petition for Inter Partes Review of U.S. Pat. No. 8,375,957—IPR2015-00098, Exhibit 1014, PCT application No. PCT/CN2007/ 001576, filed on May 15, 2007, and Jan. 15, 2009 Chinese Declaration re CN Patent Application No. 200620090805 ("Hon '805"), Oct. 21, 2014.
Logic Technology Products, Inc., Petition for Inter Partes Review of U.S. Pat. No. 8,375,957—IPR2015-00098, Exhibit 1015, '957 patent file history, Oct. 29, 2008 Preliminary Amendment, Oct. 21, 2014.
Logic Technology Products, Inc., Petition for Inter Partes Review of U.S. Pat. No. 8,375,957—IPR2015-00098, Exhibit 1016, '957 patent the history, Oct. 5, 2010, Office Action, Oct. 21, 2014.
Logic Technology Products, Inc., Petition for inter Partes Review of U.S. Pat. No. 8,375,957—IPR2015-00098, Exhibit 1017, '957 patent the history, Mar. 7, 2011, Response to Office Action, Oct. 21, 2014.
Logic Technology Products, Inc., Petition for Inter Partes Review of U.S. Pat. No. 8,375,957—IPR2015-00098, Exhibit 1018, '957 patent the history, Mar. 29, 2011, Applicant's "Marked-Up Specification", Oct. 21, 2014.
Logic Technology Products, Inc., Petition for inter Partes Review of U.S. Pat. No. 8,375,957—IPR2015-00098, Exhibit 1019, '957 patent the history, Jun. 8, 2011, Office Action, Oct. 21, 2014.
Logic Technology Products, Inc., Petition for inter Partes Review of U.S. Pat. No. 8,375,957—IPR2015-00098, Exhibit 1020, '957 patent the history, Dec. 8, 2011, Request for Continued Examination, Oct. 21, 2014.
Logic Technology Products, Inc., Petition for Inter Partes Review of U.S. Pat. No. 8,375,957—IPR2015-00098, Exhibit 1021, '957 patent the history, Jan. 9, 2012, Office Action, Oct. 21, 2014.
Logic Technology Products, Inc., Petition for Inter Partes Review of U.S. Pat. No. 8,375,957—IPR2015-00098, Exhibit 1022, '957 patent the history, May 9, 2012, Amendment, Oct. 21, 2014.
Logic Technology Products, Inc., Petition for Inter Partes Review of U.S. Pat. No, 8,375,957—IPR2015-00098, Exhibit 1023, '957 patent the history, Aug. 7, 2012, Office Action, Oct. 21, 2014.
Logic Technology Products, Inc., Petition for Inter Partes Review of U.S. Pat. No. 8,375,957—IPR2015-00098, Exhibit 1024, '957 patent the history, Aug. 29, 2012, Amendment, Oct. 21, 2014.
Logic Technology Products, Inc., Petition for Inter Partes Review of U.S. Pat. No. 8,375,957—IPR2015-00098, Exhibit 1025, '957 patent the history, Dec. 17, 2012, Notice of Allowance., Oct. 21, 2014.
Logic Technology Products, Inc., Petition for Inter Partes Review of U.S. Pat. No. 8,375,957—IPR2015-00098, Exhibit 1026, '957 patent the history, Jul. 2, 2013, Certificate of Correction, Oct. 21, 2014.
Logic Technology Products, Inc., Petition for Inter Partes Review of U.S. Pat. No. 8,375,957—IPR2015-00098, Exhibit 1027, U.S. Pat. No. 8,156,944 (Hon; Aerosol Electronic Cigarette), Oct. 21, 2014.
Logic Technology Products, Inc., Petition for Inter Partes Review of U.S. Pat. No. 8,375,957—IPR2015-00098, Exhibit 1028, Decision—Institution of Inter Partes Review in IPR2013-00387, Paper 7, Oct. 21, 2014.
Logic Technology Products, Inc., Petition for Inter Partes Review of U,S, U.S. Pat. No. 8,375957—IPR2015-00098, Exhibit 1029, Curriculum Vitae of Gregory Buckner, Ph.D., Oct. 21, 2014.
NJOY, Inc. et al, Petition for Inter Partes Review of U.S. Pat. No. 8,863,752—IPR2015-01301, May 29, 2015.
NJOY, Inc. et al, Petition for Inter Partes Review of U.S. Pat. No. 8,863,752—IPR2015-01301, Exhibit 1001, U.S. Pat, No. 8,863,752 ("the '752 patent"), May 29, 2015.
NJOY, Inc. et al, Petition for Inter Partes Review of U.S. Pat. No. 8,863,752—IPR2015-01301, Exhibit 1002, Declaration Samir Nayfeh, Ph.D, ("Nayfeh Decl."), May 29, 2015.

(56) References Cited

OTHER PUBLICATIONS

NJOY, Inc. et al, Petition for Inter Partes Review of U.S. Pat. No. 8,863,752—IPR2015-01301, Exhibit 1003, Canadian Pat. App. No. 2,752,134 ("Hon '134"), May 29, 2015.

NJOY, Inc. et al, Petition for Inter Partes Review of U.S. Pat. No. 8,863,752—IPR2015-01301, Exhibit 1004, U.S. Pat, No. 3,200,819 ("Gilbert"), May 29, 2015.

NJOY, Inc. et al, Petition for Inter Partes Review of U.S. Pat. No. 8,863,752—IPR2015-01301, Exhibit 1005, U.S. Pat, No. 6,155,268 ("Takeuchi"), May 29, 2015.

NJOY, Inc. et al, Petition for Inter Partes Review of U.S. Pat. No. 8,863,752—IPR2015-01301, Exhibit 1006, U.S Pat. No. 1,446,087 ("Griffin"), May 29, 2015.

NJOY, Inc. et al, Petition for Inter Partes Review of U.S. Pat. No. 8,863,752—IPR2015-01301, Exhibit 1007, Markman Hearing/Claim Construction Order, Fontem Ventures, B.V. v. NJOY, Inc., No. 14-cv-1645, Dkt. 133 (C.D. Cal. May 7, 2015), May 29, 2015.

NJOY, Inc. et al, Petition for Inter Partes Review of U.S. Pat. No. 8,863,752 IPR2015-01301, Exhibit 1008, Rulings on Claim Construction, Fontem Ventures, B.V. v. NJOY, Inc., No. 14-cv-1645, Dkt. 65 (C.D. Cal. Jan. 29, 2015), May 29, 2015.

NJOY, Inc. et al, Petition for Inter Partes Review of U.S. Pat. No. 8,863,752—IPR2015-01301, Exhibit 1009, Joint Claim Construction and Prehearing Statement, Fontem Ventures, B.V v. NJOY, Inc., No. 14-cv-1645, Dkt. 93 (C.D. Cal. Mar. 19, 2015), May 29, 2015.

NJOY, Inc. et al, Petition for Inter Partes Review of U.S. Pat. No. 8,863,752—IPR2015-01301, Exhibit 1010, Revised Joint Claim Construction and Prehearing Statement, Fontem Ventures, B.V. v. NJOY, Inc., No. 14-cv-1645, Dkt. 34 (C.D. Cal. Sept, 30, 2014), May 29, 2015.

NJOY, Inc. et al, Petition for Inter Partes Review of U.S. Pat. No. 8,863,752—IPR2015-01301, Exhibit 1011, Curriculum Vitae of Samir Nayfeh, Ph.D., May 29, 2015.

NJOY, Inc. et al., Defendants' Joint Invalidity Contentions, Case No. CV-14- 01645 etc., Feb. 26, 2015.

NJOY, Inc. et al., Defendant's Joint Invalidity Contentions, CV14-01645 etc., Exhibit D—Claim Charts for Patent 8863752, Feb. 26, 2015.

Techpowerup, www.techpowerup.com—"What is a MOSFET, what does it look like, and how does it work?"—published May 24, 2004 (Collins Report Exhibit 78).

USPTO, Final Office Action for U.S. Appl. No. 12/226,819, Jun. 8, 2011.

USPTO, Non-Final Off ice Action for U.S. Appl. No. 12/226,819, Aug. 7, 2012.

USPTO, Non-Final Office Action for U.S. Appl. No. 12/226,819, Jan. 9, 2012.

USPTO, Nora-Final Office Action for U.S. Appl. No. 12/226,819, Oct. 5, 2010.

USPTO, Non-Final Office Action for U.S. Appl. No. 13/915,427, Mar. 21, 2014.

USPTO, Notice of Allowance for U.S. Appl. No. 12/226,819, Dec. 17, 2012.

USPTO, Notice of Allowance for U.S. Appl. No. 13/915,427, Aug. 19, 2014.

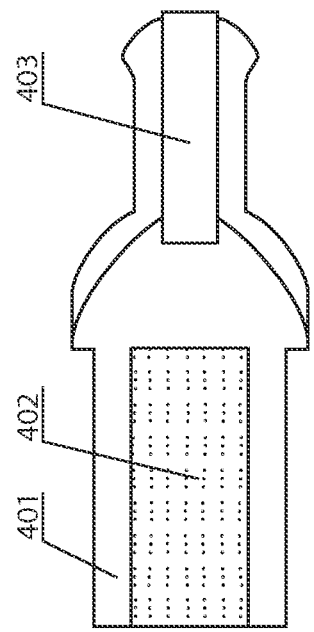
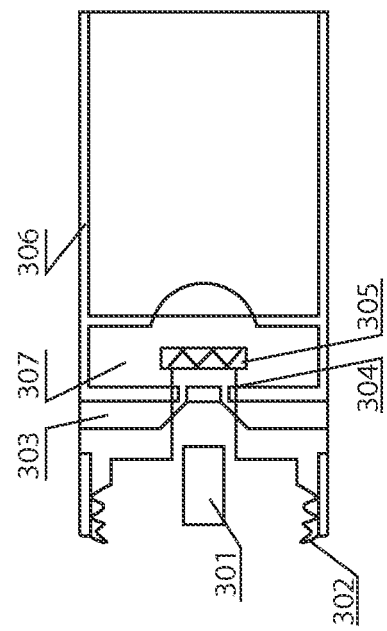
Figure 3
Figure 4

ELECTRONIC CIGARETTE

CROSS-REFERENCE TO RELATED APPLICATIONS

This application is a continuation of U.S. patent application Ser. No. 12/226,819, filed Jan. 15, 2009 and now pending, which is a 371 national phase application of International Patent Application No. PCT/CN2007/001576, filed May 15, 2007 and now converted, which claims the benefit of Chinese Patent Application No. 200620090805.0, filed May 16, 2006. All of these applications are incorporated herein by reference in their entirety.

BACKGROUND

Although smoking causes serious respiratory diseases and cancers, it is difficult to get smokers to quit smoking. Nicotine is the effective ingredient in cigarettes. Nicotine is a micromolecular alkaloid which is basically harmless to humans at low dosages. Tar is the major harmful substance in tobacco. Tobacco tar contains thousands of ingredients, dozens of which are carcinogenic.

Cigarette substitutes have used relatively pure nicotine in patches, chewing gum and aerosols. Still disadvantages remain with cigarette substitutes or products for helping smokers to quit smoking.

SUMMARY OF THE INVENTION

An improved electronic cigarette has a battery assembly, an atomizer assembly and a cigarette bottle assembly. The battery assembly connects with one end of the atomizer assembly, and the cigarette bottle assembly is inserted into the other end of the atomizer assembly, thus forming one cigarette type or cigar type body. Use of the electronic cigarette reduces cancer risks and fire hazards while providing a simulated smoking experience.

BRIEF DESCRIPTION OF DRAWINGS

FIG. 3 is the diagram of the atomizer assembly.
FIG. 4 is the diagram of the cigarette bottle assembly.

DETAILED DESCRIPTION OF THE DRAWINGS

Figure 1:
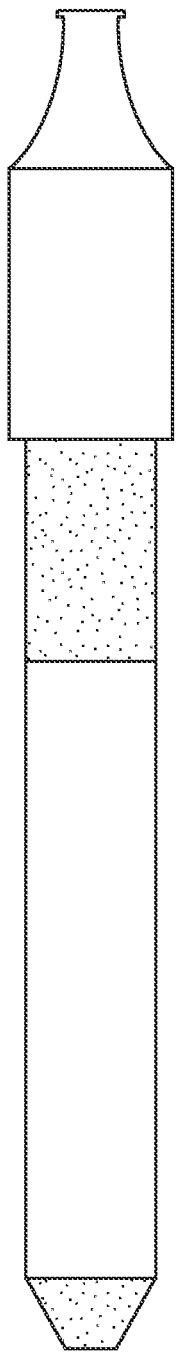
FIG. 1 is a side view of an electronic cigarette.
Figure 2A:
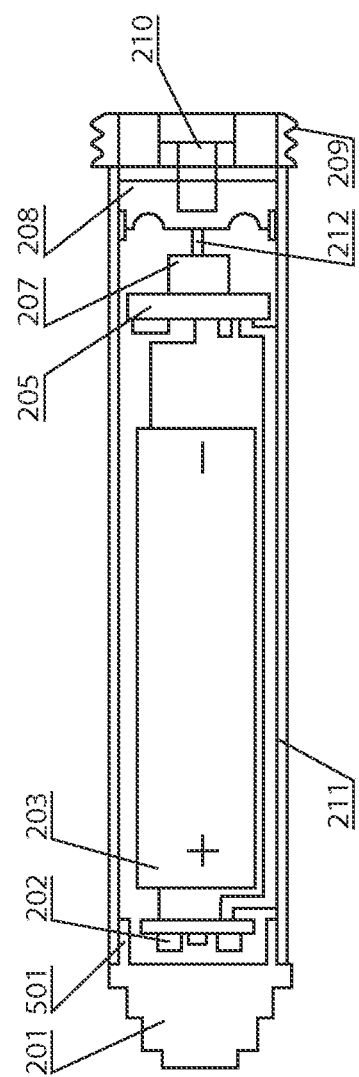
FIG. 2A is a view of the battery assembly.

As shown in FIG. 1, an electronic cigarette has an appearance similar to a cigarette inserted into the cigarette holder. As shown in FIG. 2A, the electronic cigarette includes a battery assembly, an atomizer assembly and a cigarette bottle assembly. An external thread electrode (209) is located in one end of the battery assembly, and an internal thread electrode (302) is located in one end of the atomizer assembly. The battery assembly and atomizer assembly are connected through the screw thread electrode into an electronic cigarette. The cigarette bottle assembly is inserted into the other end of atomizer assembly.

As shown in FIG. 2A, the battery assembly includes an indicator (202), lithium ion battery (203), MOSFET electric circuit board (205), sensor (207), silica gel corrugated membrane (208), primary screw thread electrode (209), primary negative pressure cavity (210), and primary shell (211). On one end of the primary shell (211) is an external thread electrode (209). On the other end is an indicator (202), where there is an indicator cap (201) on one side having a small hole (501). On the other side, the lithium ion battery (203) and MOSFET (Metallic Oxide Semiconductor Field Effect Tube) electric circuit board (205) are connected successively. The sensor (207) is located on MOSFET electric circuit board (205). Between the primary screw thread electrode (209) and sensor (207) is a silica gel corrugated membrane (208), on which there is the primary negative pressure cavity (210). The sensor (207) is connected with the silica gel corrugated membrane (208) through the switch spring (212).

The sensor (207) may be switch sensor made of elastic alloy slice, a linear output Hall sensor, a semiconductor force-sensitive chip, a semiconductor matrix thermoelectric bridge chip, capacitance or inductance sensor. The indicators (202) include two red LEDs. The lithium ion battery (203) may be either a rechargeable polymer lithium ion battery or a rechargeable lithium ion battery. The external thread electrode (209) is a gold-coated stainless steel or brass part with a hole drilled in the center. The silica gel corrugated membrane (208) may alternatively be made of fluorinated rubber, butyronitrile rubber, or elastic alloy film.

As shown in FIG. 3, the atomizer assembly includes the internal thread electrode (302), air-liquid separator (303), atomizer (307) and the secondary shell (306). One end of the secondary shell (306) is inserted into the cigarette bottle assembly for connection, while the other end has an internal thread electrode (302), in which there is the secondary negative pressure cavity (301). The air-liquid separator (303) and the atomizer (307) are connected with the internal thread electrode (302) successively. On the secondary shell (306), there is an air intake hole (502). The air-liquid separator (303) is made of stainless steel or plastic with a hole. The internal thread electrode (302) is a gold-coated stainless steel or brass part with a hole in the center.

Figure 8:
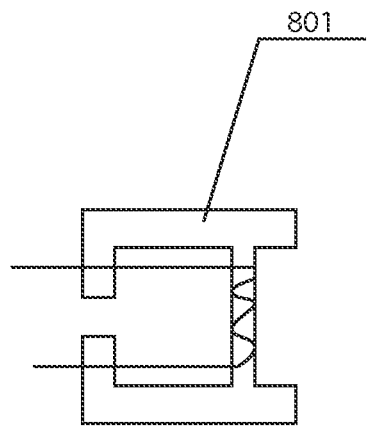
FIG. 8 is a side view of an atomizer.
Figure 9:
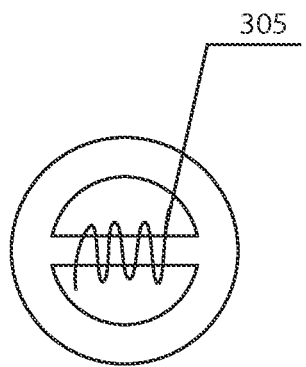
FIG. 9 is an end view of the atomizer shown in FIG. 8.
Figure 10:
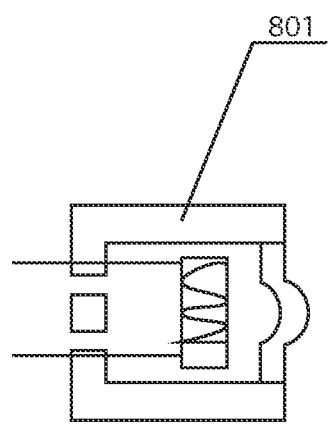
FIG. 10 is a diagram of a spray atomizer.
Figure 11:
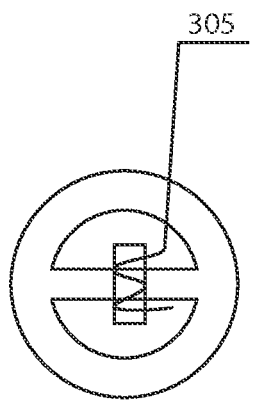
FIG. 11 is an end view of the atomizer shown in FIG. 10.

The atomizer (307) may be a capillary impregnation atomizer as in FIGS. 8 and 9, or a spray atomizer as in FIGS. 10 and 11. As shown in FIG. 4, the cigarette bottle assembly includes the cigarette liquid bottle (401), fiber (402) and suction nozzle (403). The fiber (402) containing cigarette liquid is located on one end of the cigarette liquid bottle (401). This end is inserted into the secondary shell (306) and lies against the atomizer (307). The suction nozzle (403) is located on the other end of the cigarette liquid bottle (401). Between the fiber (402) and interior wall of the cigarette liquid bottle (401) is an air intake hole (503).

Figure 5A:
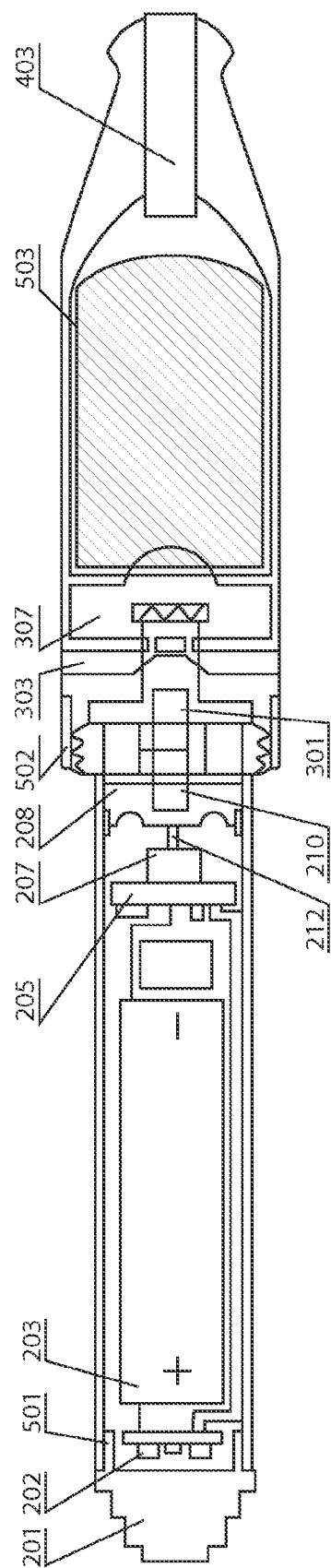
FIG. 5A is a section view of an electronic cigarette.

As shown in FIG. 5A, the standby state has the fully charged battery assembly shown on FIG. 2A fastened onto the atomizer assembly shown on FIG. 3, which is then inserted into the cigarette bottle assembly shown in FIG. 4. When the user slightly sucks the suction nozzle (403), negative pressure forms on the silica gel corrugated membrane (208) through the air intake hole (503) and the primary and secondary negative pressure cavities (210, 301). The silica gel corrugated membrane (208), under the action of suction pressure difference, distorts to drive the switch spring (212) and sensor (207), thus switching MOSFET electric circuit board (205). At this moment, the indicators (202) are lit gradually; the lithium ion battery (203) electrifies the heating body (305) inside the atomizer (307) through MOSFET electric circuit board (205) as well as the internal and external thread electrodes (302, 209).

The heating body (305) inside the atomizer (307) produces heat. The fiber (402) inside the cigarette liquid bottle (401) contains cigarette liquid, which soaks the micro-porous ceramics (801) inside the atomizer through the fiber (402). The air enters through the air intake hole (502), passes through the run-through hole on the air-liquid separator (303), and helps to form air-liquid mixture in the spray nozzle (304) of the atomizer (307). The air-liquid mixture sprays onto the heating body (305), gets vaporized, and is quickly absorbed into the airflow and condensed into aerosol, which passes through the air intake hole (503) and suction nozzle (403) to form white mist type aerosol.

When suction stops, the switch spring (212) and sensor (207) are reset; the atomizer (307) stops working; the indicators (202) gradually die down. When the operation times reaches the pre-set value, the atomizer (307) provides a work delay of 5-20 seconds per time, so as to remove the micro-dirt accumulated on the heating body (305).

Besides the micro-porous ceramics, the liquid supply material of the atomizer (307) may also be foamed ceramics, micro-porous glass, foamed metal, stainless steel fiber felt, terylene fiber, nylon fiber, nitrile fiber, aramid fiber or hard porous plastics. The heating body (305) is made of the micro-porous ceramics on which nickel-chromium alloy wire, iron-chromium alloy wire, platinum wire, or other electro thermal materials are wound. Alternatively, it may be a porous component directly made of electrically conductive ceramics or PTC (Positive Temperature Coefficient) ceramics and associated with a sintered electrode. The surface of the heating body (305) is sintered into high-temperature glaze to fix the zeolite grains, which are made of natural zeolite, artificial non-organic micro-porous ceramics or aluminum oxide grains. The cigarette liquid bottle (401) and suction nozzle (403) in the cigarette bottle assembly are made of non-toxic plastic. The fiber (402) inside of them is made of polypropylene fiber or nylon fiber to absorb cigarette liquid. In the battery assembly, there is a fine hole (501) on the indicator cap (201) for balancing the pressure difference on both sides of the silica gel corrugated membrane (208).

The cigarette liquid contains 0.1-3.5% nicotine, 0.05-5% tobacco flavor, 0.1-3% organic acid, 0.1-0.5% stabilizer, and propanediol for the remaining.

The primary and secondary shells (211, 306) are made of stainless steel tube or copper alloy tube with baked-enamel coating of real cigarette color.

Figure 12:
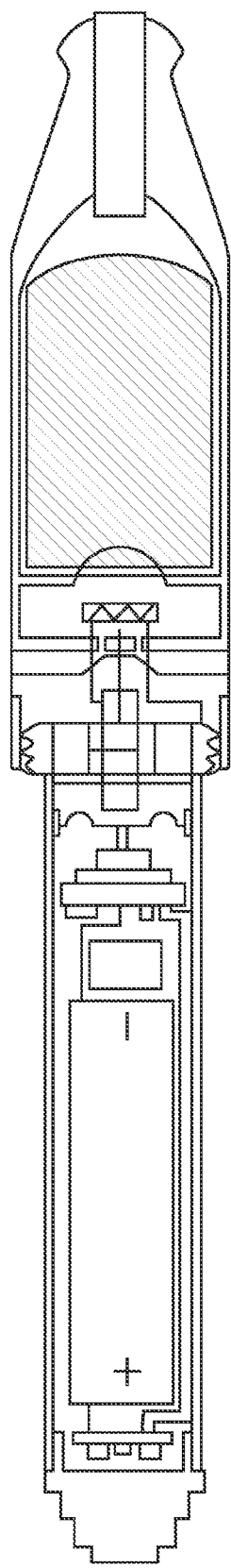
FIG. 12 is a section view of another embodiment.

As shown in FIG. 12, the diameter of the battery assembly may be increased in proportion, so that it is consistent with the diameter of the atomizer assembly. Its shell may be decorated with the leaf veins and sub-gloss brown-yellow baked-enamel coating, to create a cigar type device.

For charging the lithium ion battery (203), the screw thread electrode (601) matches the external thread electrode (209) on the battery assembly, so that it may be used as the charging interface.

Figure 2B:
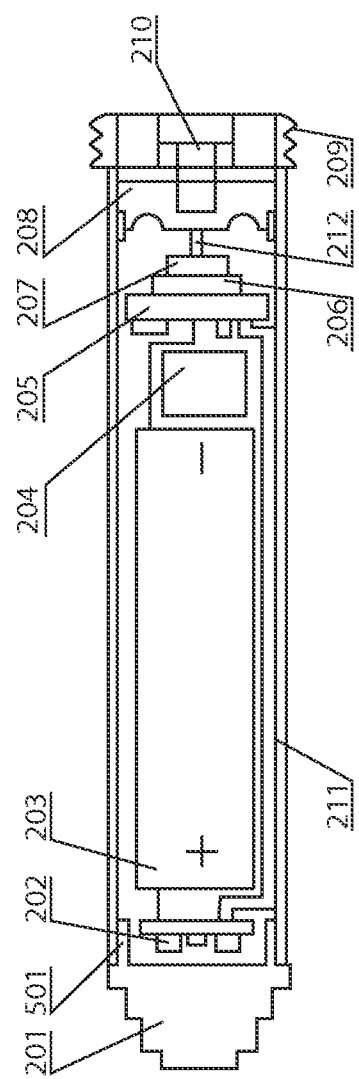
FIG. 2B is a view of another battery assembly.

The design in FIG. 2B is difference from the design in FIG. 1A as follows: Microcircuit (206) is added between MOSFET electric circuit board (205) and sensor (207). On the surface of the primary shell (211), there is a screen (204) for display of the power of the lithium ion battery (203) and the sucking times.

Figure 5B:
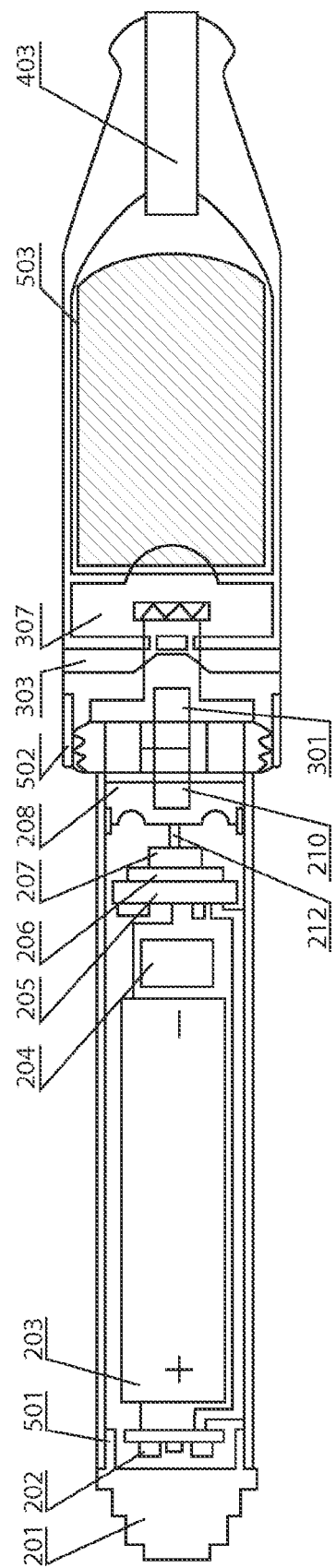
FIG. 5B is a section view of another embodiment.
Figure 6:
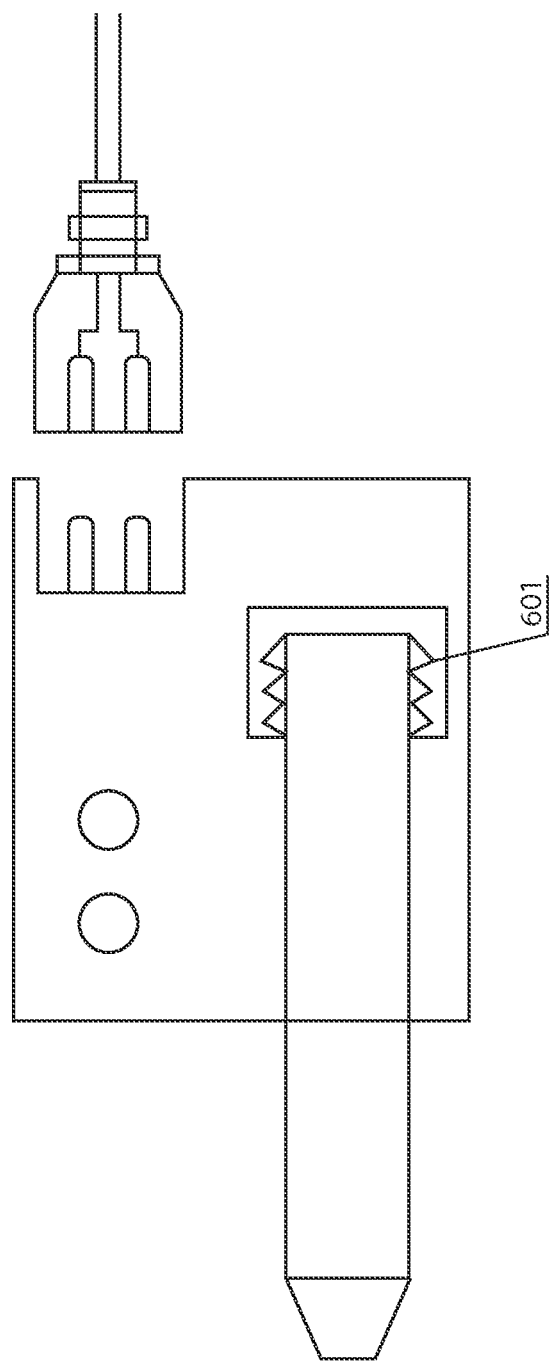
FIG. 6 is a diagram of a charger.

As shown in FIG. 5B, a fully charged battery assembly is attached onto the atomizer assembly, which is then inserted into the cigarette bottle assembly shown on FIG. 4. When the user slightly sucks the suction nozzle (403), negative pressure forms on the silica gel corrugated membrane (208) through the air intake hole (503) and the primary and secondary negative pressure cavities (210, 301). The silica gel corrugated membrane (208), under the action of suction pressure difference, distorts to drive the switch spring (212) and sensor (207), thus activating the Microcircuit (206) and MOSFET electric circuit board (205). At this moment, the indicators (202) are lit gradually; the lithium ion battery (203) electrifies the heating body (305) inside the atomizer (307) through MOSFET electric circuit board (205) as well as the internal and external thread electrodes (302, 209), so that the heating body (305) inside the atomizer (307) produces heat.

The fiber (402) inside the cigarette liquid bottle (401) contains cigarette liquid, which soaks the micro-porous ceramics (801) inside the atomizer through the fiber (402). The air enters through the air intake hole (502), passes through the run-through hole on the air-liquid separator (303), and helps to form air-liquid mixture in the spray nozzle (304) of the atomizer (307). The air-liquid mixture sprays onto the heating body (305), gets vaporized, and is quickly absorbed into the airflow and condensed into aerosol, which passes through the air intake hole (503) and suction nozzle (403) to form white mist type aerosol.

Figure 7:
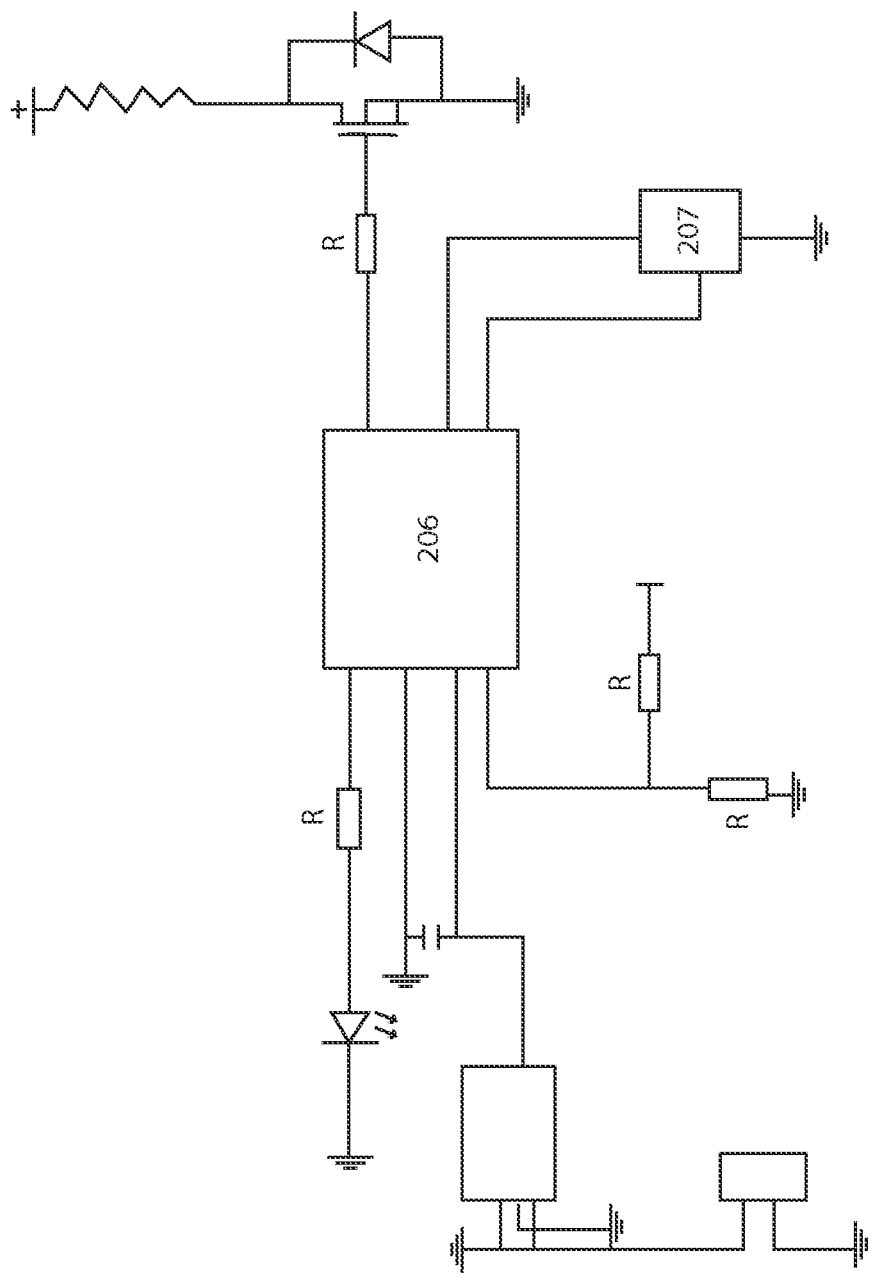
FIG. 7 is the electric circuit diagram.

As shown in FIG. 7, when the action of suction activates the sensor, Microcircuit (206) scans the sensor (207) in the power-saving mode of pulse, and according to the signal parameters of the sensor (207), restricts the atomizing capacity with the integral function of frequency to single operation time. Also, the microcircuit (206) accomplishes the pulse width modulation and over discharging protection for the constant power output, automatic cleansing for thousands of times per operation, step lighting/dying down control of the indicator, display of the operation times and battery capacity, automatic recovery after sensor malfunction shutdown, etc.

The unit and its connecting structure may also be loaded with drugs for delivery to the lung.

Above are just specifications of an example and do not necessarily restrict the scope of protection. Any equivalent modification made on the basis of the design spirit shall fall into the scope of protection.

The invention claimed is:
1. A vaporizing device comprising:
 a battery assembly comprising a battery, a sensor, an LED and a micro-controller unit electrically connected to a circuit board within a tubular battery assembly housing;
 a first electrode at an end of the battery assembly housing;
 an atomizer assembly comprising an atomizer and a liquid supply in a tubular atomizer assembly housing;
 with the atomizer including a heater wire coil wound around a porous body, with the heater wire coil and the porous body positioned perpendicular to a longitudinal axis of the tubular atomizer assembly housing;
 the heater wire coil and the porous body in an airflow path through the tubular atomizer assembly housing leading to a suction nozzle wherein air passes across the heater wire coil and the porous body;
 a second electrode at an end of the atomizer assembly housing; and
 the battery assembly and the atomizer assembly electrically connected by engagement of the first electrode with the second electrode, and with electricity conducted from the battery to the heater wire coil through the first and second electrodes.
2. The device of claim 1 with the atomizer further including a through hole aligned with the heater wire coil.

3. The device of claim 2 with the through hole centered between spaced apart wire leads of the heater wire coil.

4. The device of claim 3 with the airflow path further including an air inlet in a side wall of the tubular atomizer assembly housing at the second electrode.

5. The device of claim 3 further including fiber containing cigarette liquid in contact with the porous body.

6. The device of claim 1 with the sensor in between a pressure balancing hole in the battery assembly housing and the first electrode.

7. The device of claim 1 with the first electrode contacting the second electrode regardless of an angular orientation of the battery assembly relative to the atomizer assembly.

8. The device of claim 1 with the first electrode contacting the second electrode with the battery assembly at any angular orientation relative to the atomizer assembly.

9. A vaporizing device comprising:
a battery assembly comprising a battery, a sensor, an LED and a micro-controller unit within a tubular battery assembly housing having a pressure balancing hole on a first side of the sensor, and a first cavity in the tubular battery assembly housing on a second side of the sensor opposite from the first side of the sensor;
an atomizer assembly comprising an atomizer and a second cavity in a tubular atomizer assembly housing, with the first cavity connecting into the second cavity, the atomizer including a heater wire coil wound on a porous body, and the heater wire coil and the porous body perpendicular to a longitudinal axis of the tubular atomizer assembly housing, the heater wire coil and porous body in an airflow path through the tubular atomizer assembly housing wherein air flows across the wire coil and the porous body; and
the battery assembly and the atomizer assembly electrically connected via a first electrode at a first end of the battery assembly contacting a second electrode at a first end of the atomizer assembly with the battery assembly at any angular orientation relative to the atomizer assembly.

10. The vaporizing device of claim 9 with the airflow path passing through a through hole in the atomizer.

11. The device of claim 10 wherein the heater wire coil is on a central section of the porous body.

12. The device of claim 11 with the through hole between spaced apart wire leads of the heater wire coil.

13. The device of claim 12 with the airflow path further including an air inlet in a side wall of the tubular atomizer assembly housing adjacent to the second electrode.

14. The device of claim 12 further including fiber containing a cigarette liquid in contact with the atomizer.

15. The device of claim 12 wherein the porous body provides capillary action.

16. A vaporizing device comprising:
a battery assembly comprising battery, a sensor, and a micro-controller unit electrically connected to a circuit board within a battery assembly housing, and a first electrode at a first end of the battery assembly housing;
an atomizer assembly comprising an atomizer and liquid absorbed in fiber material in a tubular atomizer assembly housing, and a second electrode at a first end of the atomizer assembly, the atomizer including a porous body in physical contact with the fiber material, and the atomizer including a heater wire wound in a coil on a part of the porous body which is perpendicular to a longitudinal axis of the tubular atomizer assembly housing;
an airflow path through a through hole of the atomizer located between spaced apart wire leads of the heater wire coil, and the heater wire coil and the porous body in the airflow path, wherein air flows across the wire and porous body; and
the battery assembly electrically connected to the atomizer assembly via the first electrode contacting the second electrode.

17. The device of claim 16 with the airflow path further including an air inlet in a side wall of tubular atomizer assembly housing adjacent to the first end of the tubular atomizer assembly housing.

18. The device of claim 16 with the sensor in between a pressure balancing hole in the tubular battery assembly housing and the first electrode.

19. The device of claim 16 with a central axis of the through hole bi-secting the heater wire coil.

20. The device of claim 19 further including a first cavity in the battery assembly connecting into a second cavity in the atomizer assembly.

21. The device of claim 16 with the first electrode contacting the second electrode with the battery assembly at any angular orientation relative to the atomizer assembly.

22. The device of claim 21 wherein the porous body provides capillary action.

* * * * *